(12) United States Patent
Day et al.

(10) Patent No.: US 6,719,950 B2
(45) Date of Patent: Apr. 13, 2004

(54) MINIATURIZED EXHAUST GAS SENSOR

(75) Inventors: John Day, Greenville, SC (US); Jens Stefan Schneider, Anderson, SC (US); Harald Neumann, Oberriexingen (DE); Heinrich Hipp, Sigmaringen (DE)

(73) Assignee: Robert Bosch Corporation, Broadview, IL (US)

( * ) Notice: Subject to any disclaimer, the term of this patent is extended or adjusted under 35 U.S.C. 154(b) by 258 days.

(21) Appl. No.: 09/992,661

(22) Filed: Nov. 14, 2001

(65) Prior Publication Data

US 2003/0092191 A1 May 15, 2003

(51) Int. Cl.[7] .............................. G01N 7/00; G01N 9/00; G01N 27/00; H01B 13/00; C03C 25/68
(52) U.S. Cl. ............................ 422/98; 422/83; 422/88; 422/90; 422/94; 422/95; 422/96; 436/127; 436/134; 436/137; 436/139; 436/143; 436/149; 73/1.01; 73/1.02; 73/23.2; 73/23.31; 73/23.32; 73/23.42; 204/193; 204/424; 204/431; 427/58; 216/13; 216/54; 216/39; 29/592.1
(58) Field of Search ..................... 422/50, 83, 88, 422/90, 94, 95, 96, 97, 98; 436/127, 134, 137, 139, 143, 149, 151, 152, 155, 159, 160; 73/1.01, 1.02, 23.2, 23.31, 23.32, 23.42; 204/193, 424, 431; 29/592.1; 427/58; 216/13, 54, 39

(56) References Cited

U.S. PATENT DOCUMENTS

| | | |
|---|---|---|
| 4,001,758 A | 1/1977 | Esper et al. |
| 4,130,797 A | 12/1978 | Hattori et al. |
| 4,187,486 A | 2/1980 | Takahashi et al. |
| 4,228,128 A | 10/1980 | Esper et al. |
| 4,264,425 A | 4/1981 | Kimura et al. |
| 4,303,613 A * | 12/1981 | Yasuda et al. ................ 422/95 |
| 4,310,401 A | 1/1982 | Stahl |
| 4,413,502 A | 11/1983 | Ohta et al. |
| 4,540,479 A | 9/1985 | Sakurai et al. |
| 4,574,264 A | 3/1986 | Takahashi et al. |
| 4,597,850 A | 7/1986 | Takahasi et al. |
| 4,740,288 A | 4/1988 | Yamada |
| 4,786,476 A | 11/1988 | Munakata et al. |
| 4,943,330 A | 7/1990 | Iino et al. |
| 4,990,235 A | 2/1991 | Chujo |
| 5,017,340 A | 5/1991 | Pribat et al. |
| 5,139,639 A | 8/1992 | Holleboom |
| 5,270,009 A | 12/1993 | Nakamori et al. |
| 5,329,806 A | 7/1994 | McClanahan et al. |
| 5,397,442 A | 3/1995 | Wachsman |

(List continued on next page.)

Primary Examiner—Jill Warden
Assistant Examiner—Brian Sines
(74) Attorney, Agent, or Firm—Michael Best & Friedrich LLP

(57) ABSTRACT

An exhaust gas sensor includes a housing and a sensor element supported by the housing. The sensor element includes a support member having an exhaust side, a reference side, and an aperture extending through the support member between the exhaust side and the reference side. The sensor element further includes an exhaust-side electrode on the exhaust side of the support member. The exhaust-side electrode is electrically connected to a contact on the reference side of the support member via a lead extending through the aperture. The aperture is sealed around the lead such that gas cannot pass through the aperture. The support member is oriented substantially parallel to the flow of exhaust gases when the exhaust gas sensor is installed on a vehicle. The sensor further includes a contact pin in the housing that engages the contact and biases the sensor element against a portion of the housing.

26 Claims, 2 Drawing Sheets

U.S. PATENT DOCUMENTS

| | | |
|---|---|---|
| 5,423,972 A | 6/1995 | Mann et al. |
| 5,549,871 A * | 8/1996 | Kocache et al. ............... 422/95 |
| 5,670,032 A | 9/1997 | Friese et al. |
| 5,689,059 A | 11/1997 | Oh et al. |
| 5,817,920 A | 10/1998 | Kuisell et al. |
| 5,827,415 A | 10/1998 | Gur et al. |
| 5,846,391 A | 12/1998 | Friese et al. |
| 5,922,938 A | 7/1999 | Hafele |
| 5,942,092 A | 8/1999 | Weyl et al. |
| 6,063,249 A | 5/2000 | Duce et al. |
| 6,068,746 A | 5/2000 | Kojima et al. |
| 6,082,175 A | 7/2000 | Yoshikawa et al. |
| 6,164,120 A | 12/2000 | Friese et al. |
| 6,202,467 B1 * | 3/2001 | Iovdalsky et al. ............ 73/23.2 |
| 6,206,377 B1 | 3/2001 | Weyl |
| 6,266,997 B1 | 7/2001 | Nelson |
| 6,273,432 B1 | 8/2001 | Weyl et al. |
| 6,319,376 B1 | 11/2001 | Graser et al. |

* cited by examiner

MINIATURIZED EXHAUST GAS SENSOR

FIELD OF THE INVENTION

The invention relates to exhaust gas sensors, and more particularly to stoichiometric exhaust gas sensors.

BACKGROUND OF THE INVENTION

Exhaust gas sensors are well known in the automotive industry for sensing the oxygen, carbon monoxide, or hydrocarbon content of the exhaust stream generated by internal combustion engines. Stoichiometric or "Nernst"—type oxygen sensors (a widely-used type of exhaust gas sensor) measure the difference between the partial pressure of oxygen found in the exhaust gas and oxygen found in the atmosphere (reference side). By determining the amount of oxygen in the exhaust gas, the oxygen sensor enables the engine control unit to adjust the air/fuel mixture and achieve optimal engine performance.

Prior-art stoichiometric exhaust gas sensors typically include a cup-shaped sensing element or an elongated, multi-layered, bar-shaped sensing element that is supported in a housing. The sensing element typically includes a ceramic substrate, such as zirconium dioxide, that supports electrodes, heating elements, and the associated electrical leads. When the assembled sensor is mounted in the exhaust line, the ceramic element protrudes into the exhaust stream so that the exhaust-side electrode is directly exposed to and oriented substantially perpendicularly to the flow of exhaust gases. The reference-side electrode is isolated from the exhaust gas in an air-tight manner.

Zirconium dioxide, stoichiometric exhaust gas sensors can be contrasted with other types of exhaust gas sensors that operate using different fundamental principles. For example, one other well-known type of exhaust gas sensor is an amperometric or limiting current exhaust gas sensor. A limiting current sensor includes a small ceramic cavity that is hermetically sealed onto a flat solid oxide electrolyte slab. The cavity has a small hole that allows molecular oxygen to diffuse into the cavity from the environment when a DC bias is applied across the electrolyte to remove oxygen from the cavity through the solid electrolyte. A limiting current scenario is eventually reached and is governed by the rate of viscous diffusion of molecular oxygen from the environment into the cavity through the small hole. The concentration of oxygen is related linearly to the limiting current since the diffusion rate through the hole is governed by the partial pressure of oxygen in the environment outside the cavity.

Another known type of exhaust gas sensor is a titanium dioxide exhaust gas sensor. Titanium dioxide is a transition metal oxide that undergoes a change in its electrical resistance depending on the content of oxygen in the exhaust gases. The titanium dioxide (titania) is used in the form of a microscopically porously fired layer so that the exhaust gas can freely permeate into and through the mass of titania. By measuring the change in resistance of the titania, the air/fuel mixture can be maintained for optimal engine performance.

SUMMARY OF THE INVENTION

The present invention provides an improved stoichiometric exhaust gas sensor having a sensing element that is smaller and less expensive to manufacture than the prior-art cup-shaped or elongated, bar-shaped sensing elements. The smaller sensing element enables the overall size of the sensor assembly to be reduced. The sensing element is in the form of a flat disk or a flat polygonal-shaped plate (hereinafter referred to only as a disk). The exhaust-side electrode is formed on one side of the disk and the remaining components are all formed on the opposite side of the disk. A hole in the disk provides for the air-tight electrical connection between the exhaust-side electrode and the reference-side of the ceramic element. All of the electrical contacts are therefore formed on the reference-side of the disk, and electrical contact is simplified using spring-biased pin connectors or other suitable connectors supported in the housing. The configuration of the disk and the design of the housing permits the disk to be oriented substantially parallel to the flow of exhaust gases, thereby reducing the exposure of the exhaust-side electrode to water and particles that would otherwise strike the exhaust-side electrode and potentially cause poisoning and/or thermal shock problems. Sealing and insulating the disk with respect to the housing is also greatly facilitated.

More specifically, the invention provides a sensor element for an exhaust gas sensor. The sensor element includes a support member having an exhaust side, a reference side, and an aperture extending through the support member between the exhaust side and the reference side. The sensor element also includes an exhaust-side electrode on the exhaust side of the support member. The exhaust-side electrode is electrically connected to a contact on the reference side of the support member via a lead extending through the aperture. The aperture is sealed around the lead such that gas cannot pass through the aperture from the exhaust side to the reference side of the support member.

The invention also provides an exhaust gas sensor for sensing a gas in a flow of exhaust gases. The sensor includes a housing and a sensor element supported by the housing. The sensor element includes a support member having an exhaust side, a reference side, and an aperture extending through the support member between the exhaust side and the reference side. The sensor element further includes an exhaust-side electrode on the exhaust side of the support member. The exhaust-side electrode is electrically connected to a contact on the reference side of the support member via a lead extending through the aperture. The aperture is sealed around the lead such that gas cannot pass through the aperture from the exhaust side to the reference side of the support member.

In one aspect of the invention, the support member is oriented such that a substantially planar surface defined by the exhaust side is substantially parallel to the flow of exhaust gases when the exhaust gas sensor is installed on a vehicle. In another aspect of the invention, the sensor further includes a contact pin in the housing and engaged with the contact. The contact pin is biased toward the contact to maintain electrical contact with the contact. In yet another aspect of the invention the support member has a perimeter, and the contact pin is biased toward the contact to bias the support member against a portion of the housing such that exhaust gases cannot flow around the perimeter of the support member to the reference side.

The invention also provides a method of manufacturing a sensor element for an exhaust gas sensor. The method includes providing a support member having first and second sides, forming an aperture that extends between the first and second sides in the support member, forming a conductive lead that extends through the aperture, and forming an electrode on the first side of the support member and in electrical contact with the lead.

In one aspect of the invention, forming the conductive lead further includes sealing the aperture around the lead such that gas cannot pass through the aperture. In another aspect of the invention, the method further includes forming an electrode on the second side of the support member so that the electrode on the second side is electrically isolated from the lead and the electrode on the first side of the support member. In yet another aspect of the invention, the method further includes forming a heating element on the second side of the support member so that the heating element is electrically isolated from the lead and the electrodes.

Other features and advantages of the invention will become apparent to those skilled in the art upon review of the following detailed description, claims, and drawings.

Figure 1:
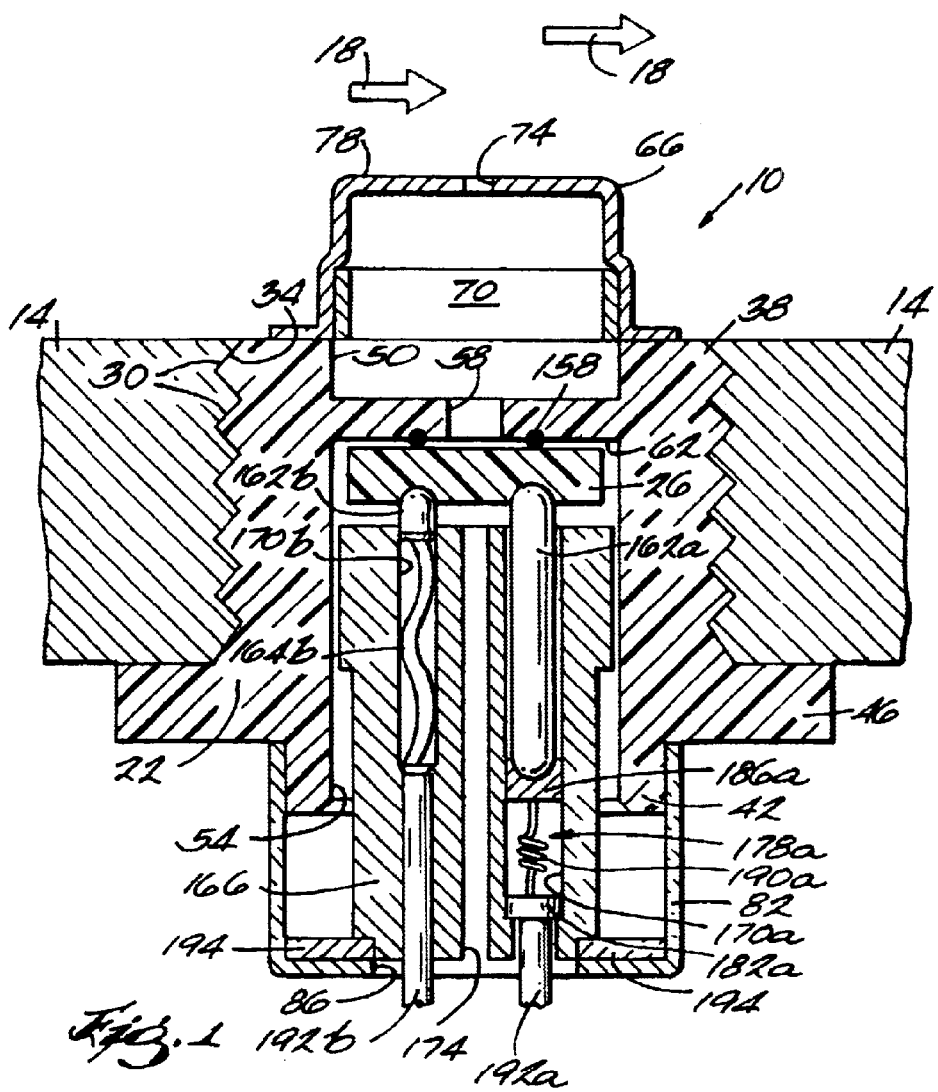
FIG. 1 is a section view of an exhaust gas sensor embodying the invention.

Before one embodiment of the invention is explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein is for the purpose of description and should not be regarded as limiting. The use of "including" and "comprising" and variations thereof herein is meant to encompass the items listed thereafter and equivalents thereof as well as additional items.

DETAILED DESCRIPTION OF THE PREFERRED EMBODIMENT

FIG. 1 illustrates a zirconium dioxide, stoichiometric exhaust gas sensor assembly 10 embodying the invention. The sensor assembly 10 is designed to be mounted on a vehicle 14 (only a portion of the vehicle is shown) adjacent the flow of exhaust gases represented by the arrows 18. While the sensor assembly 10 is illustrated as being a 4-wire design commonly used in the automotive industry, 3-wire designs for use in the automotive and marine industries, and 1-wire designs for use in the automotive and small-engine industries are also contemplated by the invention.

The exhaust gas sensor assembly 10 includes a housing 22 that supports a sensor element 26. The housing 22 is preferably made of stainless steel and includes external threads 30 configured to be received in a corresponding threaded aperture 34 in the vehicle 14. Of course, other methods of securing the housing 22 to the vehicle 14 can also be used. The housing 22 further includes an exhaust end 38 and a reference end 42. A flange 46 is preferably located adjacent the reference end 42 and acts as a stop when the housing 22 is inserted into the threaded aperture 34.

The housing 22 defines a bore extending therethrough from the exhaust end 38 to the reference end 42. The bore includes a first portion 50 adjacent the exhaust end 38, and a second portion 54 adjacent the reference end 42. A connecting portion 58 provides communication between the first and second portions 50 and 54, and has a diameter that is substantially smaller than the diameters of the first and second portions 50 and 54. The interface between the second portion 54 and the connecting portion 58 defines a seat 62, the purpose of which will be described in detail below.

A protection tube 66 is coupled to the exhaust end 38 of the housing 22 and extends into the flow of exhaust gases 18 when the sensor assembly 10 is mounted on the vehicle 14. The protection tube 66 and the first bore portion 50 together define a cavity 70. Exhaust gases 18 enter the cavity 70 through an aperture 74 formed in the protection tube 66. As seen in FIG. 1, the aperture 74 is preferably formed in an end wall 78 that is oriented substantially parallel to the direction of flow of the exhaust gases 18.

A cover tube 82 is coupled to the reference end 42 of the housing 22 and includes an aperture 86 that provides access to the second bore portion 54, as will be described in greater detail below. The protection tube 66 and the cover tube 82 can be made of any suitable materials, such as stainless steel, and can be coupled to the housing 22 in any suitable manner.

Figure 4:
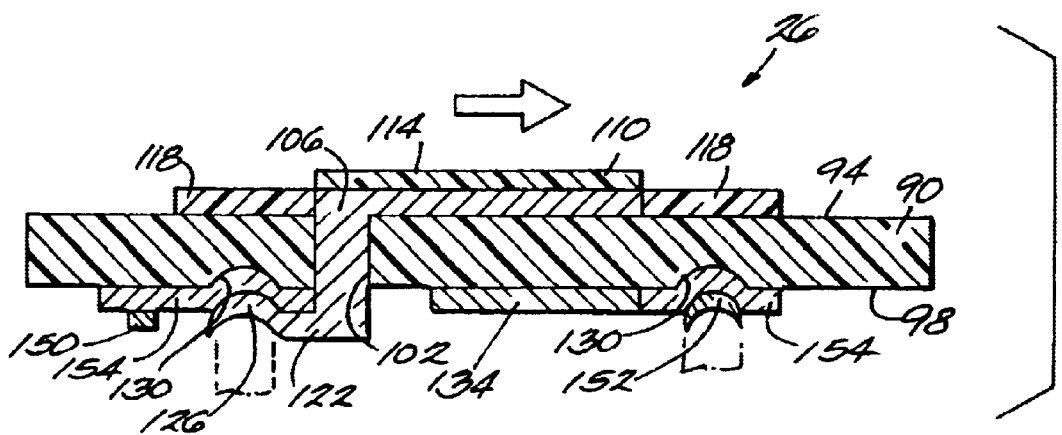
FIG. 4 is a section view taken along line 4—4 of FIG. 3.
Figure 2:
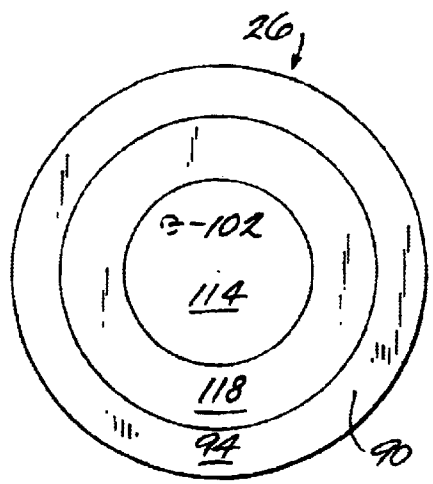
FIG. 2 is a plan view showing the exhaust side of the sensor element of the exhaust gas sensor of FIG. 1.
Figure 3:
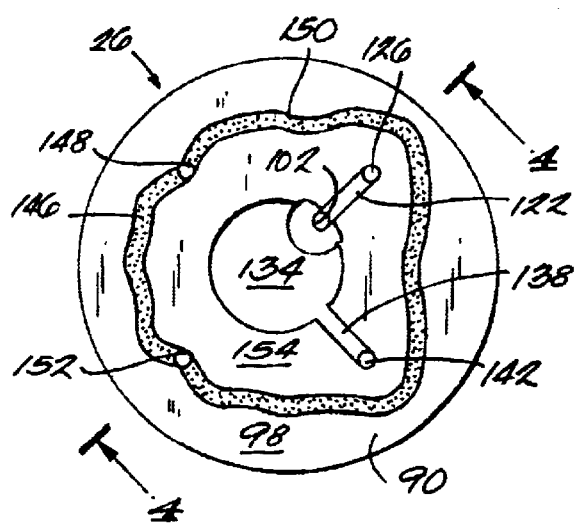
FIG. 3 is a plan view showing the reference side of the sensor element of the exhaust gas sensor of FIG. 1.

FIGS. 2, 3, and 4 illustrate the sensor element 26 in greater detail. As seen in FIGS. 2, 3, and 4 the sensor element 26 is disk-shaped and includes a support member 90 having an exhaust side 94 (see FIG. 2) and a reference side 98 (see FIG. 3). The support member 90 can be made by pressing $ZrO_2/Y_2O_3$ granulate, or is more preferably made from planar YSZ/ceramic green sheet. In FIGS. 2 and 3, the support member 90 has a diameter of approximately 1 cm, however, the diameter of the support member 90 can be smaller or larger to suit the specific application.

Figure 5:
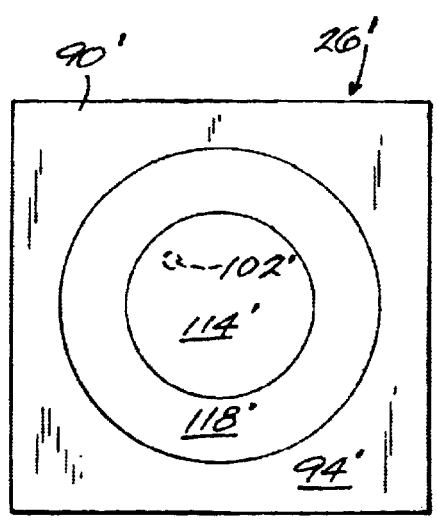
FIG. 5 is a plan view showing the exhaust side of an alternative sensor element.
Figure 6:
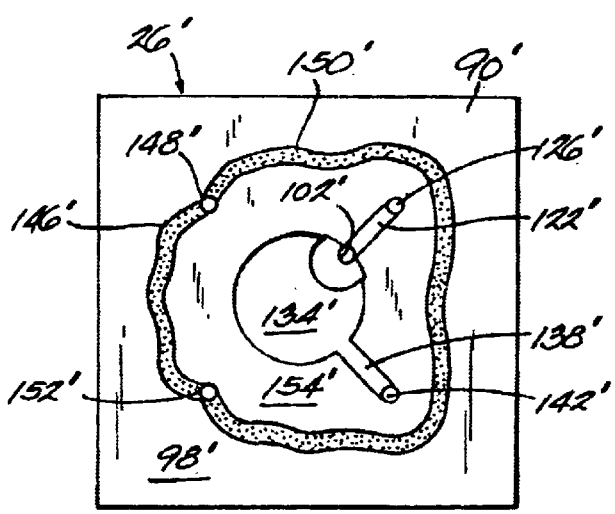
FIG. 6 is a plan view showing the reference side of the sensor element of FIG. 5.

FIGS. 5 and 6 illustrate an alternative sensor element 26' having a support member 90' that is polygonal in shape. While illustrated as being square, the support member 90' could also be other polygonal shapes, such as pentagonal, hexagonal, heptagonal, octagonal, and the like. With the exception of the shape of the support member 90, the alternative sensor element 26' is substantially the same as the sensor element 26, and only the sensor element 26 will be described in detail. Like elements on the sensor element 26' will be given like reference numerals designated as prime (').

As best seen in FIGS. 1 and 4, the exhaust side 94 defines a substantially planar surface and the reference side 98 also defines a substantially planar surface that is substantially parallel to the planar surface defined by the exhaust side 94. Before proceeding further with the description of the sensor element 26, it should be noted that FIG. 4 has been greatly enlarged and exaggerated for the purposes of description and for ease of illustration. The layers of material shown on the exhaust side 94 and the reference side 98 (which will be discussed in detail below) are illustrated as being much thicker than in actuality.

First, an aperture 102 is formed by punching, piercing, drilling, or otherwise breaking through the support member 90. The aperture 102 extends through the support member 90 between the exhaust side 94 and the reference side 98. The location of the aperture 102 in the support member 90 is not critical, and the location shown in FIGS. 2–6 is just one possible location for the aperture 102. Preferably, the aperture 102 is no greater than approximately 1 mm in diameter.

Next, a feed-through lead 106 (see FIG. 4) extending through the aperture 102 is formed via needle injection, screen printing, jet printing, or insertion of a conductive wire into the aperture. The lead 106 is preferably made of platinum or other highly conductive materials. Preferably, a platinum paste is injected into the aperture 102 or is printed over the aperture 102 to substantially fill the aperture 102. Before applying the platinum paste, it may be helpful to isolate the aperture 102 with pastes containing $Al_2O3$ or $Nb_2O_5$. The lead 106 provides a gas-tight seal between the exhaust side 94 and the reference side 98 such that no exhaust gases 18 can pass through the aperture 102 from the exhaust side 94 to the reference side 98. Gas-tightness can be accomplished in several ways after the lead 106 is formed, including sealing with glass frit over the aperture 102, sealing with glass frit in the aperture 102 and on top of the lead 106, or sealing with glass frit after firing.

After the lead 106 is formed, or possibly in the same step as the forming of the lead (if printing is used to form the lead 106), an exhaust-side electrode 110 (see FIG. 4) is formed on the exhaust side 94 of the support member 90 to be in electrical contact with the lead 106. Preferably, the exhaust-side electrode 110 is printed using a platinum paste, however, other application methods can also be used. A protective layer 114 (see FIGS. 2 and 4) is then applied over the exhaust-side electrode 110 to protect the exhaust-side electrode 110 from the environment. Again, printing or other suitable methods of material application can be used. The protective layer is preferably a porous, co-centered ceramic layer or a thermally-sprayed spinel layer. Additionally, an isolation layer 118 of alumina or other suitable insulating material is printed or otherwise applied around the outer perimeter of the exhaust-side electrode 110 to isolate the exhaust-side electrode 110 from the housing 22.

On the reference side 98 of the support member 90, a lead strip 122 (see FIGS. 3 and 4) is printed or otherwise applied to make electrical contact with the lead 106. The lead strip 122 terminates in a concave contact pad 126 that is formed due to the presence of one of a plurality of indentations 130 (see FIG. 4) that are pressed into the reference side 98 of the support member 90. The contact pad 126 completes a conductive pathway or circuit made up of the exhaust-side electrode 110, the lead 106, and the lead strip 122.

A reference-side electrode 134 is also printed or otherwise applied on the reference side 98 of the support member 90 using a platinum paste. As best seen in FIGS. 3 and 4, the reference-side electrode 134 does not come into contact with the lead strip 122. In the illustrated embodiment, the reference-side electrode 134 is printed such that a gap is left between the perimeter of the reference-side electrode 134 and the lead strip 122. Alternatively or additionally, a layer of insulating material (not shown) can be printed or otherwise applied between the lead strip 122 and the reference-side electrode 134. As seen in FIG. 3, a lead strip 138 extends from the reference-side electrode 134 and terminates in a concave contact pad 142 that is formed due to the presence of another of the plurality of pressed indentations 130.

First and second resistance heaters 146 and 150, respectively, are printed or otherwise applied in a ring around the reference side 98 of the support member 90. Preferably, the heaters 146 and 150 are screen printed as a narrow-lined meander to increase the length (mm) and resistivity (W). The heater 146 includes a concave contact pad 148 that is formed due to the presence of one of the plurality of pressed indentations 130. Likewise, the heater 150 includes a concave contact pad 152 that is formed due to the presence of another of the plurality of pressed indentations 130.

The portion of the ring defined by the heater 146 is formed using a paste (preferably a platinum paste) having a first resistance R1, while the portion of the ring defined by the heater 150 is formed using a paste (also preferably a platinum paste) having a second resistance R2. The resistances R1 and R2 are determined to obtain substantially equal temperature distribution throughout the support member 90. In the illustrated embodiment, a layer of isolating material 154, such as alumina, magnesium titanate, or similar dielectric material, is printed or otherwise applied between the heaters 146, 150 and the reference side 98 of the support member 90 to achieve electrical isolation between the heaters 146, 150 and the reference-side electrode 134. As best seen in FIG. 4, the layer of isolating material 154 also separates the lead strip 122 and the contact pad 126 from the reference side 98 of the support member 90. In alternative embodiments, the layer of isolating material 154 might be eliminated, or a separate ring-shaped heater component (not shown) could be positioned around the circumference of the support member 90 with the appropriate isolation materials.

Manufacturing of the sensor elements 26 is greatly facilitated when the support members are made from YSZ/ceramic green sheet. Multiple sensor elements 26 can be formed as described above on a single ceramic sheet. After printing all of the elements 26 on a sheet, the sheet can be pressed at high pressure to improve the flatness of the sensor elements 26 and the density of the support members 90. After pressing, the sheet can be diced into the separate sensor elements 26. If square or rectangular designs are used, razor blade dicing provides an efficient method for dicing. If disk-shaped designs are desired, a high-pressure water jet or a punch-press provides efficient dicing. Once the sensor elements 26 have been separated, the individual sensor elements 26 can be fired. This process provides for fast and efficient production of large quantities of the sensor elements 26.

It should be noted that while the order of manufacture described above is preferred, the steps can be interchanged as desired. For example, it is possible to fire the sheets or the separated support members 90 prior to printing the components of the sensor element 26. Additionally, the entire board of printed sensor elements 26 could be fired prior to the dicing operation.

As is evident from the above description, printing is the most preferable method of forming or applying the various layers on the support members 90 because it enables efficient, mass-quantity production. While screen printing is preferred, jet printing can also be used. Additionally, as noted above with respect to the protective layer 114, spraying techniques can also be used to apply some or all of the layers to the support member 90. Furthermore, the specific pastes and sprays used to create the layers can be the same as those being used on prior art sensor assemblies, or can be modified or optimized as desired.

The sensor element 26 is assembled in the housing 22 as shown in FIG. 1. First, the sensor element 26 is inserted into the second bore portion 54 at the reference end 42 until the exhaust side 94 of the sensor element 26 engages the seat 62. As shown in FIG. 1, a seal in the form of an sealing ring 158 is partially recessed into the seat 62 and engages the exhaust side 94 of the sensor element 26 to substantially prevent the flow of exhaust gases 18 around the perimeter of the support member 90. In other words, exhaust gases 18 that enter the second bore portion 54 through the connecting portion 58 are confined to the area directly adjacent the exhaust-side electrode 110 and within the confines of the sealing ring 158. The sealing ring 158 is preferably made of a temperature-resistant material, such as stainless steel plated with a soft cover material. The soft cover material can be copper or other suitable materials.

It should be noted that the design of the housing 22 or the sensor element 26 could be modified so that no sealing ring 158 is necessary. For example, the exhaust side 94 of the support member 90 could include a circular ridge that would achieve the same function as the sealing ring 158. Alternatively, the housing 22 could be formed to include a circular ridge integral with the seat. Furthermore, it is possible that the interface between the seat 62 and the sensor element 26 could be gas-tight without the need for any ridge or sealing ring.

In addition to being sealed against the flow of exhaust gases 18 around the perimeter of the support member 90, exhaust gases 18 likewise cannot flow through the aperture 102 from the exhaust side 94 to the reference side 98. As described above, the aperture 102 is sealed in a gas-tight manner to prevent the flow of exhaust gases 18 from the exhaust side 94 to the reference side 98. Therefore, the reference side 98 is completely isolated from the exhaust gases 18.

In the illustrated embodiment, the sensor element 26 is both held in place against the seat 62 and electrically contacted by ceramic or metallic pins 162 (only two of the four total pins are shown). The number of pins 162 will vary depending on the type of sensor assembly (1-wire, 3-wire, or 4-wire) being used. The pins 162 are preferably coated with platinum or other conductive materials for both conductivity and resistance to corrosion. Each pin 162 contacts a respective one of the contact pads 126, 142, 148, and 152. The contact ends of the pins 162 are rounded to conform with the concavity of the contact pads 126, 142, 148, and 152, and thereby resist moving out of contact with or eroding the contact pads 126, 142, 148, and 152. As shown in FIG. 1, the contact pads 126, 142, 148, and 152, the pins 162, and the sealing ring 158 are substantially aligned to minimize the bending forces created in the support member 90.

The pins 162 are supported in the second bore portion 54 by a spacer bushing insulator 166 that is retained in the second bore portion 54 by the cover tubing 82. The spacer bushing insulator 166 is preferably made of a ceramic material, such as alumina or cordierite, that will help insulate the sensor element 26 from the remainder of the sensor assembly 10. The specific dimensions of the spacing bushing insulator 166 can be varied depending on the desired insulating requirement.

Each pin 162 is housed in a pin bore 170 formed in the spacer bushing insulator 166. The spacer bushing insulator 166 also includes a reference-air bore 174 that provides reference air to the reference-side electrode 134. Each pin 162 is spring-loaded to be biased into engagement with the sensor element 26. FIG. 1 illustrates two possible methods of achieving the spring bias.

The pin 162a (shown on the right in FIG. 1) is housed in a pin bore 170a having a diameter that is substantially larger than the diameter of the pin 162a so that the pin 162a remains substantially perpendicular to the sensor element 26 and substantially isolated from vibrations. A spring assembly 178a biases the pin 162a against the sensor element 26, and includes a spring seat 182a, a pin support member 186a, and a spring 190a coupled between the spring seat 182a and the pin support member 186a to bias the pin support member 186a, and therefore the pin 162a, toward the sensor element 26. The spring 190a can be any suitable spiral spring or flat spring. Each element of the spring assembly 178a is conductive to complete the electrical pathway to the wire 192a extending from the pin bore 170a.

The pin 162b (shown on the left in FIG. 1) is housed in a pin bore 170b. The pin 162b is metallic and includes a compressible and resilient serpentine body portion 164b that facilitates keeping the pin 162b from moving within the pin bore 170b and helps to evenly distribute the contact force over each of the pins 162b. The pin 162b completes the electrical pathway to the wire 192b extending from the pin bore 170b. Of course, other suitable designs for the pins 162 and the biasing of the pins 162 can also be used. For example, the pins 162 could be any one of a variety of known "pogo-pin" configurations.

The spring biasing of the pins 162 provides the compression load required to create the gas-tight seating of the sensor element 26 against the seat 62, and more specifically against the sealing ring 158. Additional compression loading is provided using a disk spring 194 positioned between the spacer bushing insulator 166 and the cover tube 82. Of course, the disk spring 194 can be eliminated if the pins 162 provide a suitable amount of compression loading. Alternatively, the pins 162 could be fixed relative to the spacer bushing insulator 166 such that the disk spring 194 would supply all of the necessary compression loading by biasing the spacer bushing insulator 166 toward the sensor element 26. With yet another alternative, contact to the sensor can be made by permanently adhering a wire or pin to each contact, resulting in a fixed connection that is stable at high temperatures.

As shown in FIG. 2, the exhaust side 94 of the sensor element 26, and therefore the exhaust-side electrode 110, is oriented substantially parallel to the flow of exhaust gases 18 and does not protrude into the exhaust stream 18. This orientation greatly improves the thermal shock resistance by minimizing the exposure of the sensor element 26 to liquid water in the exhaust gases 18. Furthermore, poisoning sensitivity is also reduced since particles in the exhaust gases 18 will not strike the exhaust side 94 of the sensor element 26.

Various features of the invention are set forth in the following claims.

What is claimed is:

1. A sensor element for an exhaust gas sensor, the sensor element comprising:

a support member having an exhaust side, a reference side, and an aperture extending through the support member between the exhaust side and the reference side; and an exhaust-side electrode on the exhaust side of the support member, the exhaust-side electrode being electrically connected to a contact on the reference side of the support member via a lead extending through the aperture.

2. The sensor element of claim 1, wherein the aperture is sealed around the lead such that gas cannot pass through the aperture from the exhaust side to the reference side of the support member.

3. The sensor element of claim 1, wherein the exhaust side defines a substantially planar surface and the reference side defines a substantially planar surface.

4. The sensor element of claim 1, wherein the support member is disk-shaped.

5. The sensor element of claim 4, wherein the disk-shaped support member has a diameter of approximately 1 cm.

6. The sensor element of claim 1, wherein the support member is polygonal-shaped.

7. The sensor element of claim 1, further comprising a reference-side electrode on the reference side of the support member.

8. The sensor element of claim 1, further comprising a heating element on the reference side of the support member.

9. The sensor element of claim 1, wherein the support member is ceramic.

10. The sensor element of claim 1, wherein the aperture has a diameter no greater than approximately 1 mm.

11. An exhaust gas sensor for sensing a gas in a flow of exhaust gases, the sensor comprising:
a housing; and
a sensor element supported by the housing, the sensor element including
a support member having an exhaust side, a reference side, and an aperture extending through the support member between the exhaust side and the reference side; and
an exhaust-side electrode on the exhaust side of the support member, the exhaust-side electrode being electrically connected to a contact on the reference side of the support member via a lead extending through the aperture.

12. The exhaust gas sensor of claim 11, wherein the aperture is sealed around the lead such that gas cannot pass through the aperture from the exhaust side to the reference side of the support member.

13. The exhaust gas sensor of claim 11, wherein the exhaust side defines a substantially planar surface and wherein the reference side defines a substantially planar surface.

14. The exhaust gas sensor of claim 13, wherein the support member is oriented such that the substantially planar surface defined by the exhaust side is substantially parallel to the flow of exhaust gases when the exhaust gas sensor is installed on a vehicle.

15. The exhaust gas sensor of claim 11, wherein the support member is disk-shaped.

16. The exhaust gas sensor of claim 11, wherein the support member is polygonal-shaped.

17. The exhaust gas sensor of claim 11, wherein the sensor element further includes a reference-side electrode on the reference side of the support member.

18. The exhaust gas sensor of claim 11, wherein the sensor element further includes a heating element on the reference side of the support member.

19. The exhaust gas sensor of claim 11, wherein the support member is ceramic.

20. The exhaust gas sensor of claim 11, wherein the support member has a perimeter and is biased against a portion of the housing such that exhaust gases cannot flow around the perimeter of the support member to the reference side.

21. The exhaust gas sensor of claim 11, further including a contact pin in the housing and engaged with the contact, the contact pin being biased toward the contact to maintain electrical contact with the contact.

22. The exhaust gas sensor of claim 21, wherein the support member has a perimeter, and wherein the contact pin is biased toward the contact to bias the support member against a portion of the housing such that exhaust gases cannot flow around the perimeter of the support member to the reference side.

23. A method of manufacturing a sensor element for an exhaust gas sensor, the method comprising:
providing a support member having first and second sides;
forming an aperture that extends between the first and second sides in the support member;
forming a conductive lead that extends through the aperture; and
forming an electrode on the first side of the support member and in electrical contact with the lead.

24. The method of claim 23, wherein forming the conductive lead further includes sealing the aperture around the lead such that gas cannot pass through the aperture.

25. The method of claim 23, further comprising:
forming an electrode on the second side of the support member, the electrode on the second side being electrically isolated from the lead and the electrode on the first side of the support member.

26. The method of claim 23, further comprising:
forming a heating element on the second side of the support member, the heating element being electrically isolated from the lead and the electrode.

* * * * *